United States Patent
Magnusson et al.

(10) Patent No.: US 11,306,293 B2
(45) Date of Patent: Apr. 19, 2022

(54) METHOD FOR VIRUS PROPAGATION

(71) Applicant: Cytiva Sweden AB, Uppsala (SE)

(72) Inventors: Ann-Christin Magnusson, Uppsala (SE); Mats Lundgren, Uppsala (SE); Eva Blanck, Uppsala (SE); Christine Sund Lundstrom, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 42 days.

(21) Appl. No.: 16/737,390

(22) Filed: Jan. 8, 2020

(65) Prior Publication Data
US 2020/0216820 A1 Jul. 9, 2020

(51) Int. Cl.
| | |
|---|---|
| *A61K 31/7088* | (2006.01) |
| *A61K 35/18* | (2015.01) |
| *A61K 38/17* | (2006.01) |
| *A61K 39/00* | (2006.01) |
| *A61K 39/385* | (2006.01) |
| *C12N 7/00* | (2006.01) |
| *C12N 5/071* | (2010.01) |
| *C12N 9/88* | (2006.01) |
| *C12N 15/86* | (2006.01) |

(52) U.S. Cl.
CPC ............. *C12N 7/00* (2013.01); *C12N 5/0686* (2013.01); *C12N 9/88* (2013.01); *C12N 15/86* (2013.01); *A61K 39/00* (2013.01); *C12N 2720/12331* (2013.01); *C12N 2720/12343* (2013.01); *C12N 2720/12351* (2013.01)

(58) Field of Classification Search
CPC .............. A61K 2300/00; A61K 38/177; A61K 38/1774; A61K 31/7088; A61K 35/18
See application file for complete search history.

(56) References Cited

FOREIGN PATENT DOCUMENTS

| WO | 03/076462 A1 | 9/2003 |
| WO | 2014/032082 A1 | 3/2014 |
| WO | WO2014032082 | * 3/2014 |

OTHER PUBLICATIONS

Great Britain Search Report for GB Application No. 1900250.0 dated May 24, 2020 (6 pages).
Great Britain Search Report for GB Application No. 1905829.6 dated Aug. 14, 2020 (6 pages).

* cited by examiner

*Primary Examiner* — Barry A Chestnut
(74) *Attorney, Agent, or Firm* — Eversheds Sutherland (US) LLP

(57) ABSTRACT

The present invention relates to a method for virus propagation. More closely the invention relates to a method for animal component free propagation and production of rotavirus (RV) using recombinant trypsin.

10 Claims, 3 Drawing Sheets

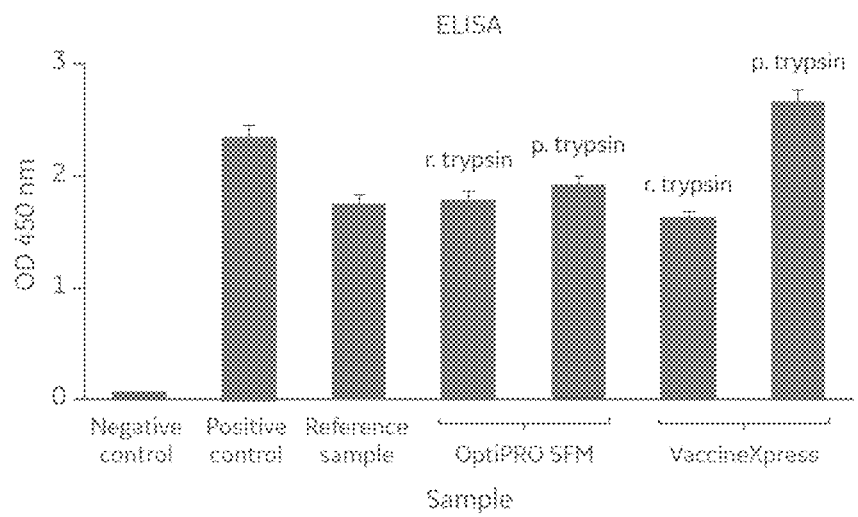
Figure 1
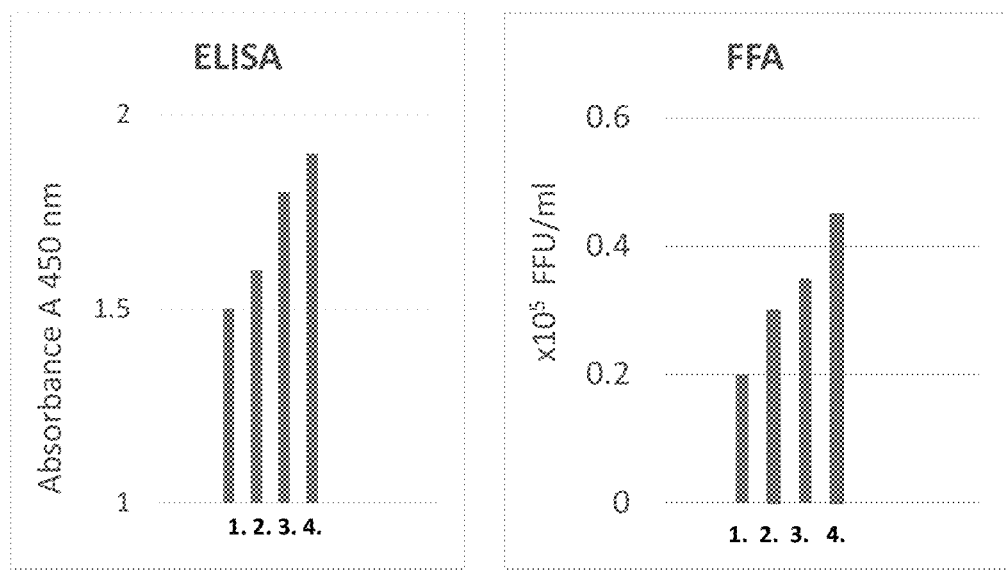
Figure 2a
Figure 2b

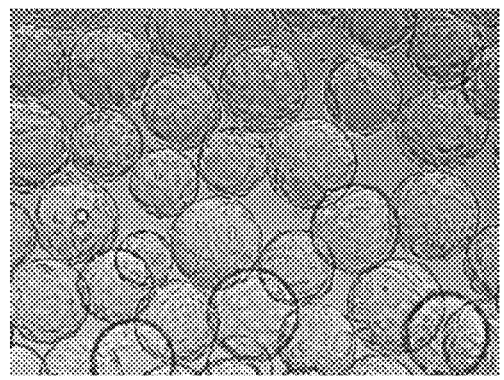
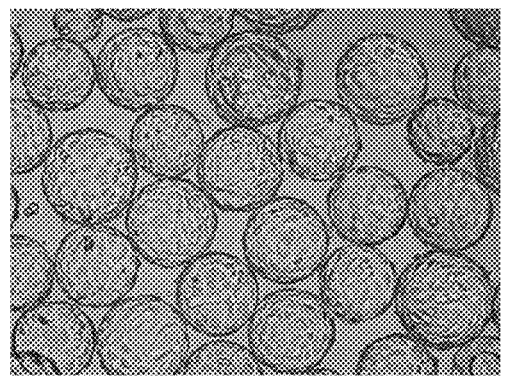
Figure 3a                Figure 3b
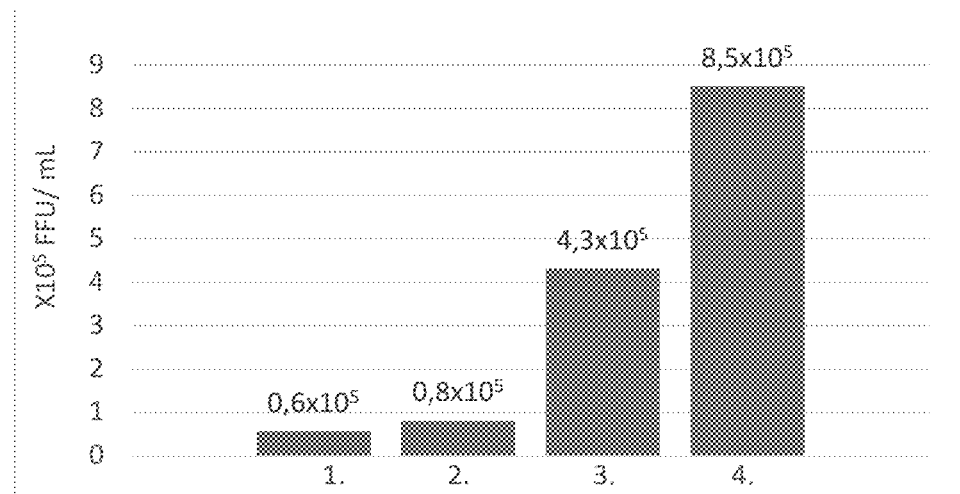
Figure 4

METHOD FOR VIRUS PROPAGATION

CROSS-REFERENCE TO RELATED APPLICATIONS

This application claims priority from United Kingdom patent application GB1900250.0, filed on Jan. 8, 2019, and United Kingdom patent application GB1905829.6, filed on Apr. 26, 2019. The entire content of the priority applications are fully incorporated by reference herewith.

Field of the Invention

The present invention relates to a method for virus propagation. More closely the invention relates to a method for animal component free propagation and production of rotavirus (RV) using recombinant trypsin for virus activation and propagation.

BACKGROUND OF THE INVENTION

Rotavirus (RV) are intestinal pathogens that infect mostly infants and young children under five years with acute diarrhea. About 600 000 children die every year from rotavirus, mainly in developing countries. The first efforts to develop a rotavirus vaccine began in the early 1980s and two of the vaccines used today are Rotarix (GSK), which is a monovalent vaccine and RotaTeq (Merck), which is a pentavalent vaccine. To propagate human RV, cultivation has been done through the use of primary and transformed monkey kidney cells and by proteolytic activation of the virus with trypsin prior to infection.

Today the RV production is done in T-flasks, cell factories or roller bottles using Vero cells as a cell substrate and porcine trypsine for activation of the RV. However, it is important to note that different RV strains differ in their capacity to infect and replicate in cell culture. One of the most important things is to preserve the structure of the RV and to maintain all three protein layers of the virus particle to keep the RV infectious.

The virus protein (VP) have different roles in the replication cycle and one role is the activation step. This is done by trypsin cleavage of VP4, that leads to virus penetration.

All current procedures for RV production require animal derived trypsin for proteolytic virus activation. It would be desirable to have an animal component free procedure and a new process for RV production in the future.

SUMMARY OF THE INVENTION

The present inventors have provided an animal component free process for RV production using recombinant trypsin.

In a first aspect the invention relates to a method for rotavirus (RV) production comprising the following steps: cell cultivation in a bioreactor, infection of the cells with RV by activation with recombinant trypsin, and RV propagation within said bioreactor in the presence of recombinant trypsin for maintenance/propagation.

The cell cultivation is preferably performed in VaccinExpress medium.

The bioreactor may be a T-flask or spinner flask or a disposable bag on a rocking platform, preferably a WAVE bioreactor, or a stirred tank.

Preferably the cell cultivation is performed on microcarriers. Most preferred the microcarriers are sterilized microcarriers, preferably Cytodex gamma.

The trypsin concentration is about 10 µg/ml for RV activation and about 5 µg/ml for maintenance/propagation without microcarriers and about 20 µg/ml for RV activation and about 7 µg/ml for maintenance/propagation when microcarriers are used.

Preferably the cells are Vero cells.

In a second aspect, the invention relates to use of the RV produced according to the method of the invention for formulation of a vaccine against rotavirus caused disease. Another use of the RV produced according to the method of the invention is for viral vector for gene therapy.

BRIEF DESCRIPTION OF THE DRAWINGS

FIG. 1 shows a diagram of total RV production with the use of different culture conditions, as detected by ELISA.

FIGS. 2a and 2b show ELISA and FFA results, respectively, indicating improvements of RV detection and infectious RV titer when the concentration of recombinant trypsin was increased during the activation and maintenance step to support RV propagation.
1. Activation 10 ug/mL, Maintenance 3 ug/mL
2. Activation 10 ug/mL, Maintenance 5 ug/mL
3. Activation 10 ug/mL, Maintenance 7 ug/mL
4. Activation 20 ug/mL, Maintenance 7 ug/mL FIGS. 3a and 3b. Microcarriers cultivation shows same cell growth and morphology using OptiPRO SFM or VaccineXpress (FIG. 3a) TOI (72h) using OptiPRO SFM, (FIG. 3b) TOI (72h) using VaccineXpress.

FIG. 4. FFA results show that VaccineXpress promotes high RV infectious titer.
1. OptiPRO SFM/recombinant trypsin
2. OptiPRO SFM/porcine trypsin
3. VaccineXpress/recombinant trypsin
4. VaccineXpress/porcine trypsin FIG. 5. FFA results shows a successful RV infection when using animal free components and Cytodex 1 Gamma in spinner flask cultivation.
1. OptiPRO SFM/porcine trypsin
2. VaccineXpress/recombinant trypsin

DETAILED DESCRIPTION OF THE INVENTION

Figure 5:
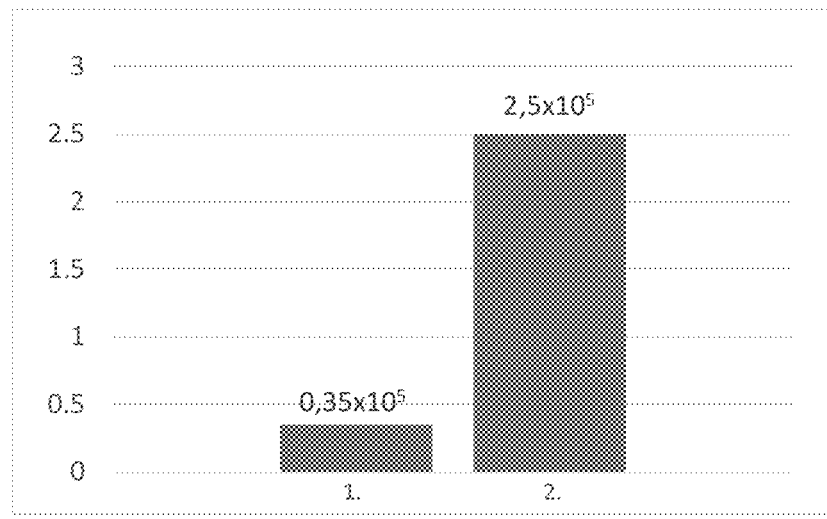

The invention will now be described more closely in association with some experiments below which were divided into two parts. The first part was to perform a screening in T-flask, where a comparison between OPTIPRO SFM/VaccineXpress medium and porcine trypsin/recombinant trypsin was done. During this part, trypsin concentration and time required to activate the virus, was evaluated and optimized to improve RV propagation.

The second part was to continue using Cytodex 1 Gamma microcarriers in spinner flask cultivation to repeat the same comparison between different medium and trypsin sources and finally a scale up process using a ReadyToProcess WAVE25 Bioreactor was done to confirm an animal component free process in single use equipment for virus production.

Terminology

| Term | Comment |
| --- | --- |
| RV | Rotavirus |
| VP | Viral Protein |
| TC | Tissue Culture |

-continued

| Term | Comment |
| --- | --- |
| CPE | Cytopathic effect |
| FBS | Fetal Bovine Serum |
| MA104 | Monkey African Green kidney cell |
| MVB | Master Virus Bank |
| WVB | Working Virus Bank |
| WCB | Working Cell Bank |
| FFU | Fluorescence Focus Unit |
| FFA | Fluorescence Focus Assay |
| ELISA | Enzyme-linked immunosorbent assay |
| MOI | Multiplicity of Infection |
| TOI | Time of Infection |
| TOH | Time of Harvest |
| SFM | Serum Free Medium |
| PBS | Phosphate Buffered Saline |
| EDTA | Ethylenediaminetetraacetic acid |
| FITC | Fluorescein isothiocyanate |
| MEM | Minimal essential Medium |

Materials/Equipment
Chemicals, Reagent and Media

| Description | Cat. Number/Vendor |
| --- | --- |
| MA104 Cells | 85102918, ATCC |
| Vero | CCL-81, ATCC |
| Rota virus | VR-2018, ATCC/Sigma Aldrich |
| MEM/EBSS | SH30024.02 (ABC212816), HyClone |
| FBS | SV30160.03 (RYL35916), HyClone |
| OPTIPRO ™SFM | 12309-19 Thermo Scientific, Lot 1722698 |
| VaccineXpress | RR16207.01 Lot RRH178741, HyClone |
| Trypsin 25 g/L | T4549-20ML (SLMB5253U), Sigma Aldrich |
| rTrypsin | 1320024671, Kerry Sheffield |
| DPBS (6x1L sterile) | D8537 6x1L Sigma Aldrich, lot RNBG0124 |
| DPBS with Ca Mg (6x1L sterile) | D8662 6x1L Sigma Aldrich, Lot RNBG1602 |
| Trypsin (0.25%) | SH30042.02 (J160004) HyClone |
| HyQtase | SV30030.01 Lot J170015 |
| BSA | A7906 Sigma Aldrich |
| PBS (Ca Mg) | SH30264.1S HyClone |
| PBS for staining procedure | BE17-516Q Lonza |
| 4% Formaldehyde solution pH 6.9 | 1.00496.5000 Sigma Aldrich |
| Triton X-100 | T9284, Sigma Aldrich |
| Tween 20 | P7949, Sigma Aldrich |
| L-glutamine | SH30034.01 HyClone |
| Pluronic F-68 | 24040-032 Thermo Fisher |
| Sigmacote | SL2-100 ml, Sigma Aldrich |
| TrypLE Select 1X | 12563-029 Thermo Fisher |
| Trypsin inhibitor | T6522 Sigma Aldrich |
| PBS-EDTA | D8537 Sigma Aldrich |
| Anti RV Antibody | C66130M Meridian |
| Goat anti mouse Ab FITC | 97022, Abcam |
| Ridascreen ® Rotavirus enzyme immunoassay | C0901 (EMM Life science) |
| Hoechst 33342 | 135-1304 (BioRad)/62249 (Thermo Fisher Scientific) |

Working Virus Bank (WVB)

Rotavirus A (VR-2018TM from ATCC) was used which is a Wa (TC adapted) strain wherein the original source was from a patient with positive RV in diarrhoea stool. A Working Virus Bank (WVB) was created by growing MA104 (ATCC) cells grown in Minimal essential medium (MEM GE Healthcare) supplemented with 5% fetal bovine serum (FBS, GE Healthcare) and 4 mM glutamine in a 2-layer Cell Factory (CF, Nunc) until the cells reached a cell density of 1.5-2×105 cells/cm2. The MA104 cells were washed once in serum-free media and the last wash was done in PBS with Ca2+ Mg2+ to remove all traces of the serum before virus infection. The dilution of rotavirus (VR2018, 1:10), porcine trypsin concentration (10 ug/ml, (Sigma Aldrich) and time for activation (1 h, 37° C.) for the cleavage of the VP4 protein. Activated rotavirus was added to the CF, enough to cover the cell layer and the cells were infected for 1 h at 37° C. with gently mixing. Upon infection, growth medium was added containing additional trypsin (5 ug/ml) to support virus infection. Daily microscopic examination of the infection was done to observe the occurrence of cytopathic effect. The CPE may have a varying appearance and can be described as refractile rounding, sloughing, cell clumping followed by lysis. Virus material was harvested by freeze-thawing three times to release virus and improve the virus yield, followed by centrifugation (2000 rpm for 10 minutes) to remove cellular debris from the harvest. The WVB was aliquoted in 50 ml Falcon tubes and stored at −80° C.

The virus material was measured using Fluorescent Focus Assay (FFA) to estimate the infectivity titer. Unfortunately the amount of infectious (triple layer) and noninfectious (double layer) particles are unknown but can be confirmed by TEM (electron microscopy).

EXPERIMENT 1

Comparison Between Cell Culture Medium and Trypsin for RV Propagation Using Vero Cells in T-Flask Cultivation Initial experiments were done in T-flasks and designed to compare two different cell culture media, (VaccineXpress and OPTIPRO™ SFM) and two different trypsin (porcine and recombinant) in T25 cultures. For activation, the virus protein (VP) for Rota have different roles in the replication cycle and one role is the activation step. This is done by trypsin cleavage of VP4 (RV attachment protein), allowing for entry of the virus into the host cell.

To activate the RV from WVB, concentration of 10 µg/ml trypsin for both porcine (Sigma Aldrich) and recombinant trypsin (KERRY Bio-Science) was used and added to the virus mix and incubated for 1 h in a 37° C. watherbath.

Vero cells were seeded and at the time of infection (TOI) was reached, the Vero cells were washed twice in PBS with Ca2+ Mg2+ before the activated RV was added to the T-flasks and the cells were infected for 1 hour during gently mixing in CO2 incubator. After incubation the inoculum was diluted with medium supplemented with trypsin (1 ug/ml) to support virus propagation. When an equivalent appearance of CPE occurred between the T-flasks, RV material was harvested. The result showed comparable results in cell growth regardless the medium, it shows when seeding 5×104 cells/cm2 cells in T flasks, the time of infection (TOI) was reached after 48 hour and the viable cell density (VCD) was 1.5-2×105 cells/cm2.

The use of recombinant trypsin for activation and RV propagation was investigated in order to develop an animal origin-free RV production process. For RV detection, ELISA (RIDASCREEN®, rotavirus enzyme immunoassay) was used which detected VP 6 antigen in all culture and in FIG. 1 small difference in total RV production was shown which indicates that possibility of a process optimization of recombinant trypsin can be achieved.

Furthermore an experiment was done to improve the RV propagation by increasing recombinant trypsin concentration where different concentration for the activation step and maintenance was tested. For activation of the RV, two concentrations of the recombinant trypsin was tested, 10 µg/ml and 20 µg/ml for 1 h at 37° C. T-25 flasks were seeded and by time of infection (TOI) was reached the activated RV was added to the T-flasks in a lower volume under gently mixing in $CO_2$ incubator for 1 hour and then the inoculum was diluted with medium using different concentrations of the recombinant trypsin (3, 5 and 7 μg/ml) to support virus propagation. When CPE occurs, RV material was harvested and RV was measured by ELISA for RV detection and FFA to determine the infectious virus titer. This experiment using VaccineXpress medium indicate that RV titer be improved by increasing recombinant trypsin concentration both for activation and maintenance to support RV propagation. Small differences in the morphology and CPE during the RV infection could be noticed. Based on analytical results in FIGS. 2*a* and 2*b*, where an increase in both RV detection (ELISA) and RV infectious particles (fluorescent focus unit/ml) was seen by increasing the concentration of recombinant trypsin. Parameters for recombinant trypsin concentration was set to 20 μg/ml for RV activation and 7 μg/ml for maintenance to support RV propagation.

EXPERIMENT 2

Comparison Between Cell Culture Medium and Trypsin for RV Propagation using Vero Cells Culture on Cytodex 1 Gamma Cytodex 1 Gamma was prepared for spinner flask using by the gamma irradiated Cytodex 1 (3 g/L) in 50 ml complete cell culture medium and allowed to equilibrate in the incubator for at least 2 hours before the Vero cells were added. Vero cells were detached from their cultivation flask, according to standard procedure Immediately after detachment, trypsin inhibitor (stock solution 1 mg/ml) was added to the cell suspension, ⅕ of the volume of HyQtase that was used. The Vero cells were counted and the start cell density was 0.3×106cells/ml, 15×106 cells used for a 50-ml spinner flask cultivation using VaccineXpress or OptiPRO SFM supplemented with 4 mM L-Glutamine and 0, 2% Pluronic F-68.

The spinner flasks were placed on the stirrer platform (Techne) in the incubator (37° C., 5% $CO_2$) under continuous stirring at 40 rpm. Approximately 50% of the medium was exchanged after 48 hours to maintain good condition. Thereafter, cell growth was followed until the time of infection (TOI) and in FIG. 3 a VCD of 1×106 (+/−0.2×106) cells/ml was reached. Samples were taken daily to determine the cell growth, viability and morphology. Cell concentration and viability was determined using cell counter NC200.

For activation of the RV WVB, porcine trypsin (10 μg/ml) or recombinant trypsin (20 μg/ml) were used for 1 h at 37° C. Vero cells were washed twice in PBS with $Ca^{2+}$ $Mg^{2+}$ by letting the microcarrier settle and media was removed as much as possible without loosing any microcarriers. After the last PBS washing step was done and removed, activated RV was added to the spinner flask, ⅓ of the total culture volume and Vero cells were infected for 1 h in the incubator (37° C., 5% $CO_2$) under continuous stirring at 40 rpm.

After the virus had infected the Vero cells, the inoculum was diluted using medium supplemented with either porcine trypsin (5 μg/ml) or recombinant trypsin (7 μg/ml) to support virus propagation. Daily microscopic examination of infection was done and when CPE occurred, the material was harvested (TOH). RV material was transferred into a 50 ml conical tube and was freeze-thawed at −80° C. three times to improve the virus yield, followed by low-speed centrifugation (2000 rpm for 10 minutes) to remove cellular debris from the harvest lysate. The clarified RV was transferred into a new 50 ml conical tube and stored at −80° C. RV material was analyzed by ELISA for RV detection and FFA to determine the infectious virus titer.

Interestingly, the use of different culture conditions for RV infectious titer seems to have a impact of RV propagation, in FIG. 4 shows difference between the cell culture medias with up to ×10 more infectious particles produced in the VaccineXpress. This suggests that the cell culture medium composition is important for Rotavirus infectivity under serum-free conditions. This was confirmed by doing an additional RV infection which shows in FIG. 5 a successful RV infection when using animal free components and Cytodex 1 Gamma in spinner flask cultivation.

EXPERIMENT 3

RV Production Using Vero Cells on Cytodex 1 Gamma in Bioreactor Culture

A ReadyToProcess WAVE 25 bioreactor, connected to one ReadyToProcess CBCU controller, was equipped with tray 20 and one 10 L cellbag. Before inoculation, the 10 L cellbag bioreactor was inflated with air and a mixture of VaccineXpress medium and Cytodex 1 Gamma microcarriers was transferred to the bioreactor and equalized at 37° C. and 5% $CO_2$. An offset pH calibration was conducted on the culture bag before cell inoculation. Cells were inoculated at a concentration of 0.4×106 cells/mL in 2 L working volume and culture was controlled at pH 7.1, 37° C. and 5% $CO_2$. Rocking motion was set to 100%.

At culture initiation, rocking speed was set to 6 rpm at an 8° angle the first 2 hours and then increased to 10 rpm at a 6° angle. Two hours after seeding, sample was taken to ensure that the cells had started to attach to the microcarriers. Thereafter, sampling was conducted every 24 h to determine cell density and morphology. Prior to sampling, rocking speed was temporarily increased for 1 min to 20 rpm to ensure a homogenous solution. After 48 or 72 h, 50% of the working volume was exchanged for fresh culture medium. When reaching a density of approximately 1 (+/−0.2)×106 cells/mL (TOI), the cells were infected with activated RV. For activation of the RV from the WVB, recombinant trypsin (20 μg/ml) was used for 1 h at 37° C.

Vero cells were washed twice in PBS with $Ca^{2+}$ $Mg^{2+}$ by letting the microcarrier settle and media was removed as much as possible without losing any microcarriers. When last PBS washing step was done and removed, activated RV was added to the WAVE, ⅓ of the total culture volume and Vero cells were infected for 1 h under continuous rocking. After the RV had infected the Vero cells, the inoculum was diluted using medium supplemented with recombinant trypsin (7 μg/ml) to support virus propagation.

Daily microscopic examination of infection was done and when CPE had occurred, the material was harvested (TOH). RV material was aliquot and transferred into flasks and were freeze-thawed at −80° C. three times, followed by low-speed centrifugation (2000 rpm for 10 minutes) to remove cellular debris from the harvest lysate. The clarified RV was transferred into a new 50 ml conical tube and stored at −80° C. RV material was analyzed by ELISA for RV detection and FFA to determine the infectious virus titer.

The results in the table show that scaling up seems to have no effect on RV production.

| Sample | FFU/ml | ELISA (OD 450) |
|---|---|---|
| Rotavirus | $5.1*10^5$ | 1.2 |
| Rotavirus ref sample | $2.6*10^5$ | 1.2 |

Based on the data from T flask and spinner flask culture, the aim was to show scalability solution for RV production using microcarriers and an animal component free materials. It was found that the Vaccine Xpress medium formulation promotes the stability of the RV to remain infectious in Bioreactor culture.

Analysis

ELISA (RIDASCREEN®, rotavirus enzyme immunoassay) for RV detection is a quantitative method.

The outcome is presented as a dilution factor, which is compared to a positive and negative control. The microwell plate is coated with a monoclonal antibody against VP6. This VP6 group is a specific antigen that is found in all rotaviruses that cause disease in humans. Presence of rotavirus in the sample, a sandwich complex will be formed consisting of immobilized antibodies, RV antigens, and antibodies conjugated with the biotin-streptavidin-peroxidase complex.

Fluorescence Focus Assay (FFA) is an infectivity method.

RV was serial diluted into a 96 well plate with MA104 cells. After RV infection, MA104 cells were labelled with an anti-RV antibody and a FITC-conjugated secondary antibody. Plates were scanned with the IN Cell Analyzer 2200 and RV infectious cells (green fluorescent cells) were counted using IN Cell Analyzer 1000 Workstation, and a titer of fluorescent focus forming units (FFU) per ml was calculated.

Conclusion

The results of the invention show that there were significant differences for infectious RV between the tested cell culture media and that recombinant trypsin can be used to replace porcine trypsin for RV production.

Pre-sterilized microcarrier cultures yielded similar cell-specific productivity as cells grown in static mode in T-flasks. Furthermore, the described culture conditions were successfully implemented for an animal component-free RV propagation in a single-use ReadyToProcess WAVE 25 bioreactor system. It is known that animal strains used in laboratory models reach titers of $10^7$ to $10^8$ per mL compared to human adapted RV strains which average titers one to three logs less than most animal strains. In the described experiments, an RV titer of $10^5$ per mL was reached for a human adapted RV strain. FIG. 5 shows the surprising result that VaccineExpress gave about 7 times better titer than conventional medium.

The present inventors have shown that infectious Rotavirus can be produced using animal origin-free raw materials. This is important from a quality and regulatory perspective as animal derived components can contain adventitious agents. It is well known that bovine serum can carry adventitious virus and there is also a concern around prions. The Rotarix vaccine was found to contain porcine circovirus and porcine circovirus DNA could also be detected in the Rotateq vaccine. It is believed that this contamination was introduced due to the use of porcine trypsin. It is not possible to reduce or inactivate adventitious agents in live virus-based vaccines. Thus, these vaccines need to be produced with raw materials and processes that minimize all possibilities to contamination. Another source of adventitious agents could be open processing of cell culture such as manual handling of cell factories or roller bottles. Furthermore, the pooling of numerous roller bottles or cell factories also make it more difficult to detect potential contamination in one of the vessels before pooling. The use of microcarriers and recombinant trypsin in the method for RV of the present invention enables RV production in closed bioreactors and means that a single batch can be harvested in high yield without the need of pooling numerous vessels.

The invention claimed is:

1. A method for rotavirus (RV) production comprising the following steps: cultivating cells in a bioreactor, infecting the cells with RV by activation with recombinant trypsin, and propagating the RV within said bioreactor in the presence of recombinant trypsin for maintenance/propagation, wherein the trypsin concentration is about 10 μg/ml for RV activation and about 5 μg/ml for maintenance/propagation.

2. The method according to claim 1, wherein the cell cultivation is performed in VACCINEXPRESS medium.

3. The method according to claim 1, wherein the bioreactor is a T-flask or spinner flask.

4. The method according to claim 1, wherein the bioreactor is a disposable bag on a rocking platform, preferably a Wave bioreactor, or a stirred tank.

5. The method according to claim 1, wherein the cell cultivation is performed on microcarriers.

6. The method according to claim 1, wherein the microcarriers are sterilized microcarriers, preferably Cytodex gamma.

7. A method for rotavirus (RV) production comprising the following steps: cultivating cells in a bioreactor, infecting the cells with RV by activation with recombinant trypsin, and propagating the RV within said bioreactor in the presence of recombinant trypsin for maintenance/propagation, wherein the cell cultivation is performed on microcarriers, and wherein the trypsin concentration is about 20 μg/ml for RV activation and about 7 μg/ml for maintenance/propagation.

8. The method according to claim 1, wherein the cells are Vero cells.

9. Use of the RV produced according to claim 1 for formulation of a vaccine against rotavirus caused disease.

10. Use of the RV produced according to claim 1 as a viral vector for gene therapy.

* * * * *